United States Patent [19]

Brännström et al.

[11] Patent Number: 4,461,186
[45] Date of Patent: Jul. 24, 1984

[54] STERILE WATER COLLECTOR

[76] Inventors: Lars Brännström, Ståthållaregatan 5, Göteborg, Sweden, 414 69; Karsten Pedersen, Torild Wulffsg. 36, Göteborg, Sweden, 413 19

[21] Appl. No.: 421,163

[22] Filed: Sep. 22, 1982

[30] Foreign Application Priority Data

Sep. 30, 1981 [SE] Sweden .................. 8105564

[51] Int. Cl.$^3$ .................. G01N 1/12; G01N 1/14
[52] U.S. Cl. .................. 73/864.62; 73/864.02; 73/864.67
[58] Field of Search .......... 73/864.62, 864.01, 864.02, 73/864.67, 864.83, 864.51, 864.11, 864.52, 863.31; 141/313, 314

[56] References Cited

U.S. PATENT DOCUMENTS 3,063,296 11/1962 Huch et al. .................. 73/864.62 X
3,176,517 4/1965 Chelminski .................. 73/864.62
3,242,740 3/1966 Niskin .................. 73/863.31
4,302,974 12/1981 Niskin .................. 73/864.62

OTHER PUBLICATIONS

ZoBell–Collector "Limnology & Oceanography", vol. 8, pp. 489–492, (1963).

Primary Examiner—S. Clement Swisher
Assistant Examiner—James R. Giebel
Attorney, Agent, or Firm—Holman & Stern

[57] ABSTRACT

A sterile water collector of the type comprising a sample device (11) and a sample receptacle (1), and in which the sample receptacle is activated by means of a dropping plummit, which brings about opening of an inlet to the evacuated sample receptacle, which consists of a flexible wall structure (6) located between two rigid end bodies (2,3), whereby the rigid end bodies by means of a load are arranged to be pulled in a direction away from each other a certain distance when the sample device (11) is activated, whereby the sample water is sucked into the receptacle.

4 Claims, 5 Drawing Figures

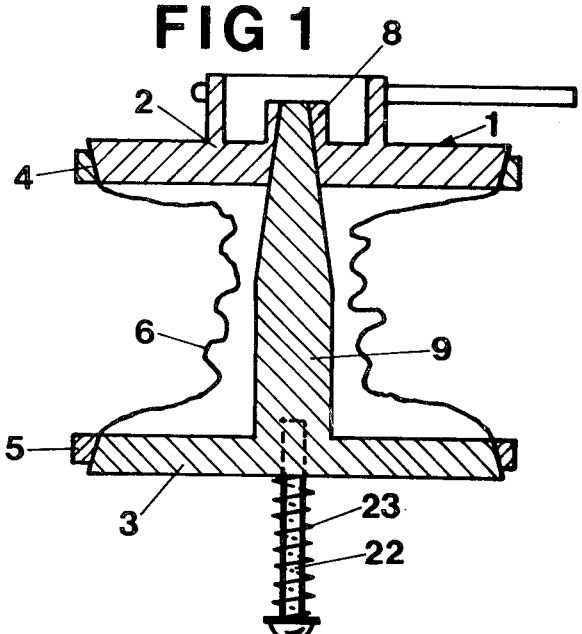
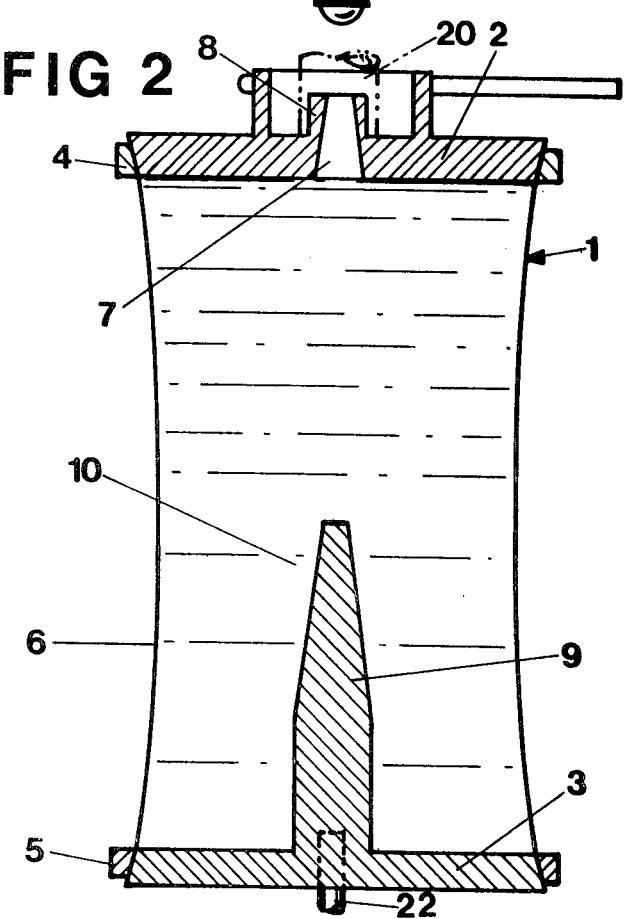

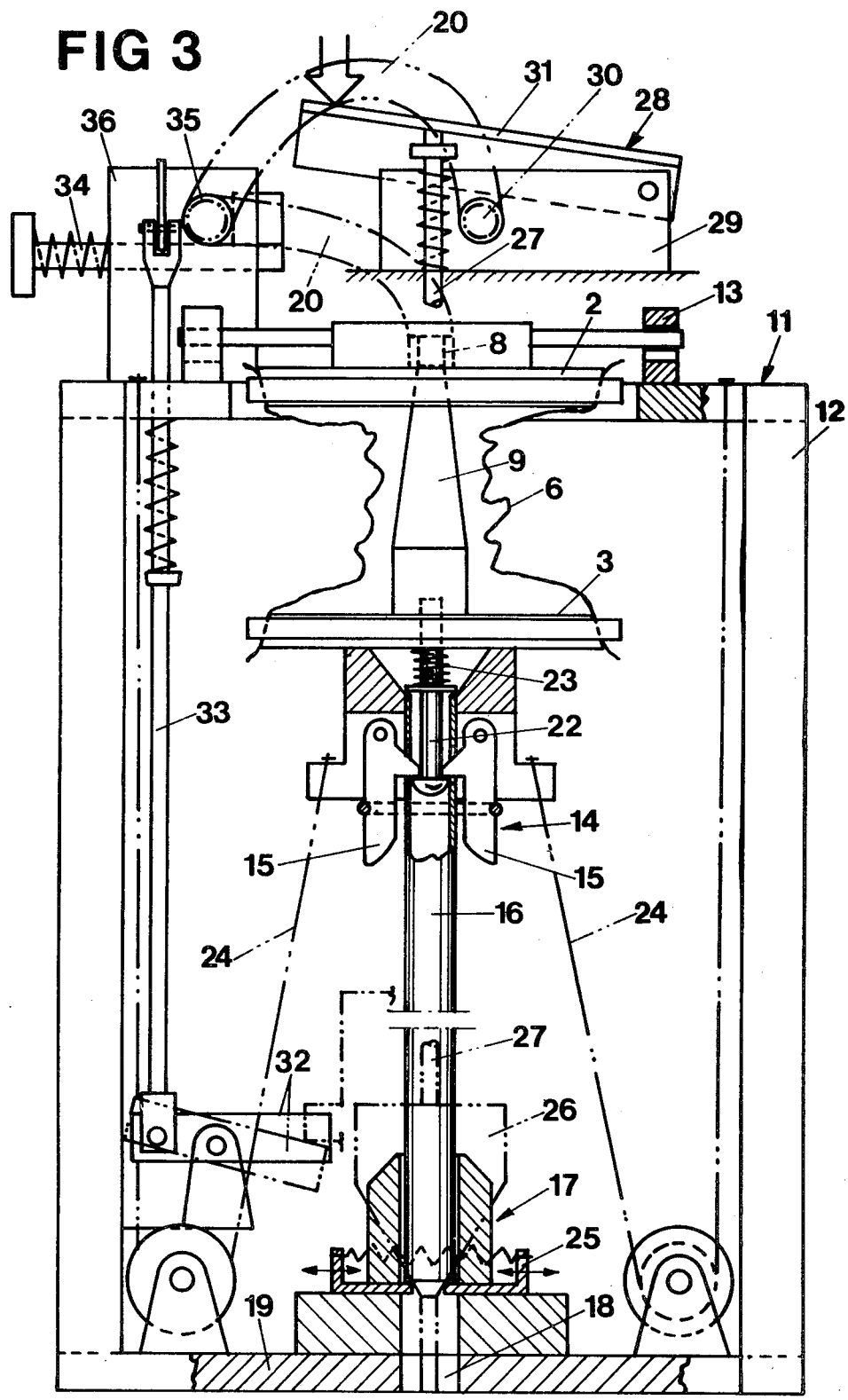

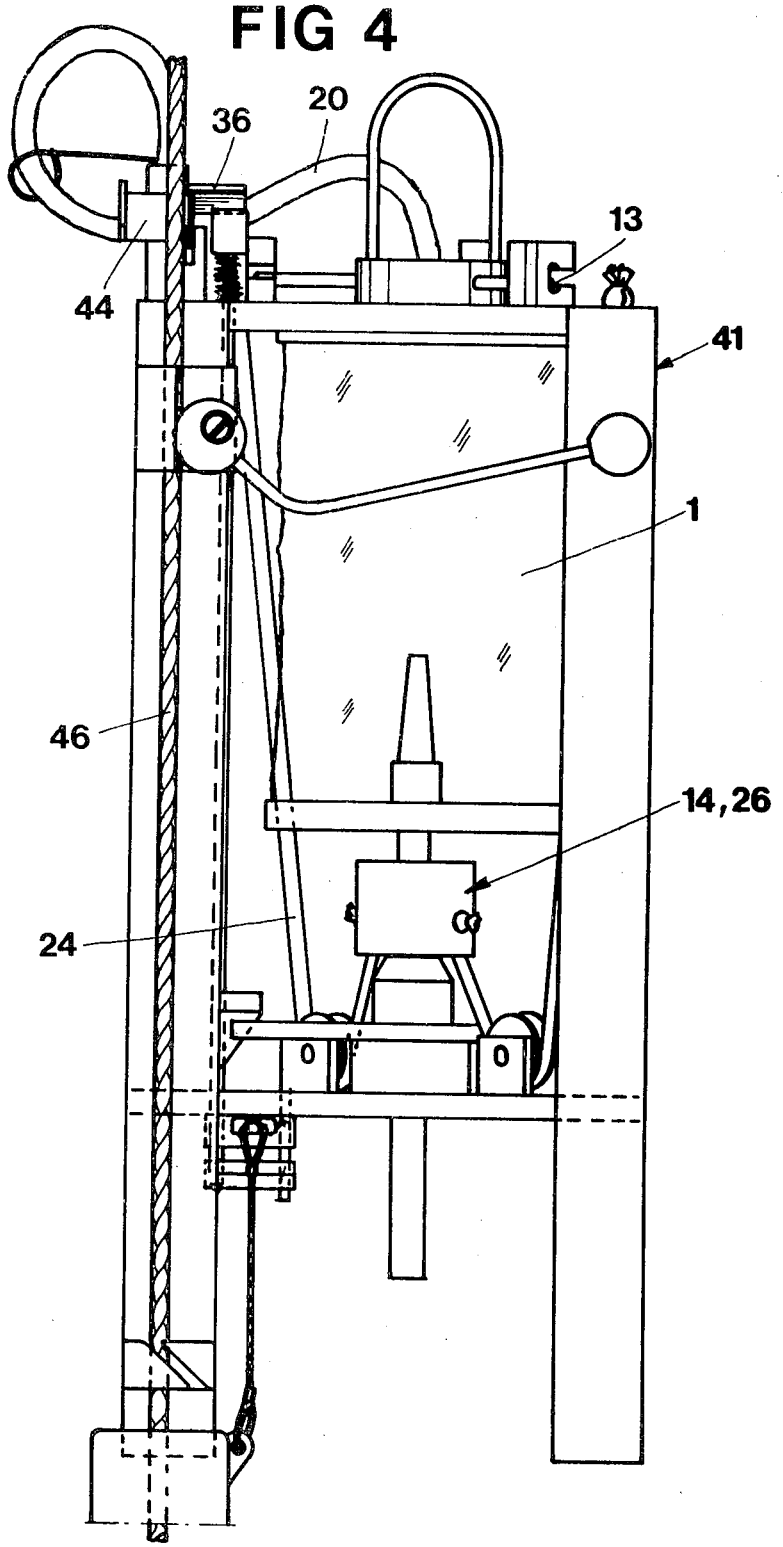

STERILE WATER COLLECTOR

BACKGROUND OF THE INVENTION

The present invention relates to a sterile water collector of the type comprising a sampling device and a sample receptacle arranged to be activated by external actuation, whereby an inlet to the evacuated sample receptacle is opened.

Sampling of water for bacteriological tests necessiates that the samples can be collected without being contaminated by foreign bacteria. Such sampling is used e.g. at bacteriological control of bathing and drinking water or for determination of the number and activity of bacteria in different water systems. Different water collectors have been designed for such purposes, but none of those conventional water collectors fulfil all requirements which are made of a practically manageable, sterile water collector. Those requirements are:

Sampling device and sample receptacle shall be separable units. It is desirable for economic reasons that several sample receptacles can be used on the same sampling device, as the sampling device for a sterile water collector requires some technical contrivances. The manageability of the sample increases further if the sample receptacle can be separated from the sampling device when recovered from the water.

The water collector shall be usable together with a wire from a winch as well as with a separate rope. A wire from a ship is commonly used, but sampling from jettys, in wells and the like necessiates that the collector can be used on a single rope.

Fitting and maneuvering of the water collector shall be realizable with simple hand grips. Such factors as rough seas, coldness and the use of clumsy gloves must not hamper the sampling work.

The sample shall be collected so far from the collector that there is no risk for contamination from the wire and sampling device. This is a requirement, as bacteria may accompany the collector and wire down through the water and then contaminate the sample, and these bacteria are not representative for the water at the sampling level if the sample is collected immediately adjacent the collector or wire.

It shall be possible to use several collectors on the same wire simultaneously, as samples are often desired from several levels at the same time. When the collector is activated by means of a plummet which runs along the wire, a second plummet is to start from a level below or above the collector just activated in order to activate the next collector etc.

The inlet for sample water shall be open only during the time for collecting the sample. If the inlet is open during the entire time of submersion or recovery the risk for contamination is of course increased.

Sampling device and receptacle shall be able to operate without problems on large depths at high pressures.

It shall be possible to sterilize the sample receptacle, preferably by means of an autoclave, which can easily be accomplished at sea.

The sample receptacle shall be a cheap disposable article or it shall be reusable after machine dish-washing.

The water collector shall be manufacturable for sample volumes between about 0.3 liters and 10 liters without the function being altered.

Sampling device and receptacle must withstand rough treatment.

For certain tests it must be possible to make the sample receptacle impermeable to light.

The collector shall withstand low temperatures. The temperature of the surface water of the sea can, during the winter, be about $-3°$ C. and the air temperature can be considerably lower. The collector should not become brittle at such temperatures.

Earlier sterile water collectors use as activating member a plummit, which is dropped along the carrying wire and which when reaching the collector by means of its kinetic energy starts the sampling.

One of these older water collectors is the ZoBell collector, which operates with a sterile and evacuated glass bottle to which is connected a rubber tube, which at one of its ends is closed by means of a glass tube. When the plummit is dropped and hits the glass tube this is broken and the rubber tube is, by means of its inherent flexibility, swung out from the sample receptacle. Water flows into the bottle and fills it. At the same time a second plummit is activated and dropped from the activated collector and is allowed to sink to the next collector etc. Advantages of this ZoBell collector are that it is easy to handle and that it collects the sample some distance away from the collector. Its drawbacks are that it can not operate on depths larger than 50-100 meters, and that the sample receptacle is open after activation.

The water collector most frequently used in microbiology is the Niskin-collector, in which a falling plummit releases a knife, which cuts a hole in a sterile plastic bag threaded over the spring-loaded wings of the collector. A rubber tube for collecting the sample then swings out a short distance from the collector, at the same time as the spring force causes the wings to be filled out, whereby the bag is filled. The bag is thereupon automatically closed by a closing mechanism. This collector has the advantages that it is closed immediately after the sampling, it can be used at great depths and large volumes can be collected. Its drawbacks are that use of the collector requires several careful hand grips made simultaneously which is time-wasting and difficult. The plastic bag is furthermore disposable and the cost for each bag is high, about 10 to 15 Swedish Krona, and at the same time as the bag is frail whereby it can easily leak at handling. Furthermore the knife which cuts off the plastic bag can contaminate the contents, and finally bigger collectors of this type are very difficult to handle.

SUMMARY OF THE PURPOSE AND MOST ESSENTIAL FEATURES OF THE INVENTION

The purpose of the invention is to provide a practically usable sterile water collector of the type initially described, which fulfils all requirements set out hereabove. This has been achieved thereby that the water collector has been given the following characteristics; the sample receptacle consists of a flexible wall structure located between two rigid end bodies, and the rigid end bodies are arranged at activation of the sampling device by means of an external force to be displaced in a direction away from each other a certain distance, whereby sample water is sucked into the receptacle.

BRIEF DESCRIPTION OF THE DRAWINGS

The invention will hereinafter be further described with reference to embodiments shown in the accompanying drawings.

FIG. 1 shows in a side view a sample receptacle forming part of the water collector according to the invention in inactivated position, FIG. 2 shows the same sample receptacle in activated position, filled with water, FIG. 3 shows in a schematic side view a water collector according to the invention in inactivated position, FIG. 4 is a side view showing a modified embodiment of a sampling device provided with a sample receptacle as shown in FIG. 2 and in activated position.

DESCRIPTION OF PREFERRED EMBODIMENTS

Figure 5:
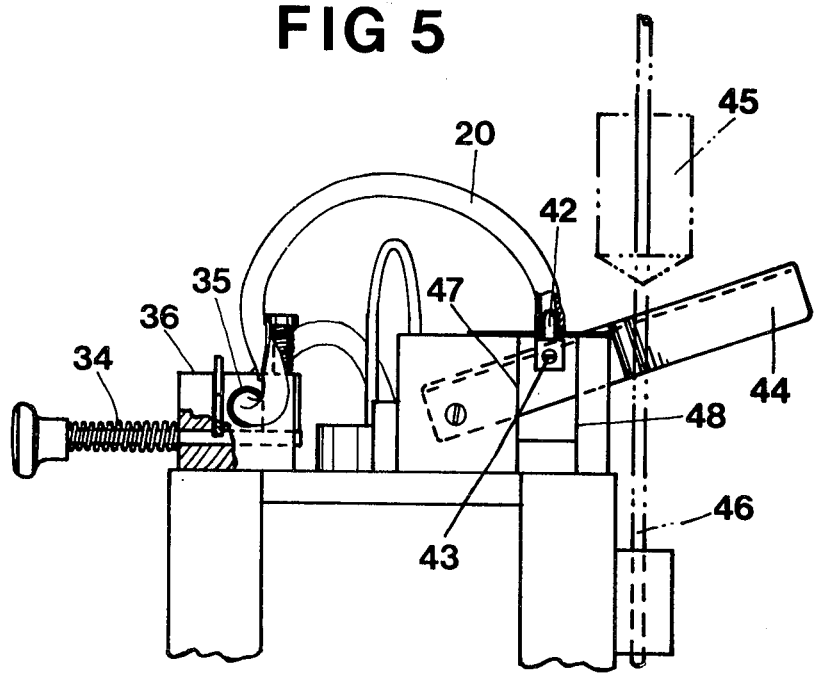
FIG. 5 shows a detail of the top part of the sampling device shown in FIG. 4 and viewed from the left hand side thereof.

The water collector according to the invention incorporates a sampling device 11 and a sample receptacle 1, shown in FIG. 1 in inactive, evacuated position, whereas FIG. 2 shows the sample receptacle 1 in activated, water-filled position.

The sample receptacle consists of an upper circular gable 2, a lower circular gable 3, upper and lower clamping rings 4,5 and a cylindrical plastic bag or hose 6. The upper gable 2 is provided with a central inlet 7 designed with a tubular socket 8 projecting from one side thereof and intended for connection of a tube 20. The through-inlet 7 is conically decreasing in a direction towards the socket 8.

The lower gable 3 is provided with a column 9 projecting from one side thereof and terminating in a tapering portion 10, having the same taper as the inlet 7.

The clamping rings 4,5 can be designed in different ways but the important thing is that they can be used for attaching one end of the plastic bag or hose 6 to the gables 2 and 3 respectively. It must be possible to sterilize the material used in the gables and in the clamping rings in an autoclave and they should withstand machine dish-washing.

The plastic hose 6 is commercially available at a price of about 1 SEK(Swedish Crown)/meter, and is in medical care technology referred to as "autoclave plastics".

At the end of the rubber tube 20 facing away from the socket 8 there is, in this embodiment, arranged a glass tube 30, the free end of which is closed, whereby also the sample receptacle 1 is closed.

Prior to the sampling the plastic bag 6 is evacuated via the rubber tube 20, which is thereupon closed by means of said glass tube. In this position the sample receptacle has the appearance shown in FIG. 1. The sample receptacle is then ready for use after treatment in an autoclave. All parts of the sample receptacle except for the glass tube, which is broken later, can be dish-washed and reused, but the plastic bag 6 should for practical reasons be considered as disposable material.

The plastic bag 6 for the sample receptacle can be cut off from a roller into desirable lengths depending on desired sample volume, but the relation between height and width is important as too large a ratio means that the bag 6 when activated will not unfold entirely and too small a ratio means that the sample receptacle can not be entirely evacuated. The design of the tapering column portion 10 and the tapering central inlet 7 provides a nonreturn valve which is essential for the function of the collector as it will prevent the plastic hose 6 from creeping into the sample tube when the sample receptacle is subjected to pressure.

In FIG. 3 is shown one embodiment of a sample device 11 with the sample receptacle 1 in inactive position. The sample device comprises a stand 12, and the upper gable of the sample receptacle can be attached to the upper part thereof in a bayonet mount 13 or the like. The lower gable 3 of the sample receptacle is provided with a coupling dowel 22 with a pressure spring 23 threaded thereon.

The coupling dowel can be inserted in a coupling 14, provided with coupling shanks 15 by means of which the sample receptacle is rigidly attached to the coupling. A mounting tube 16 extends from the coupling 14 to a releasing device 17 by means of which the mounting tube 16 can be displaced out through an opening 18 in the bottom plate 19 of the sample device. The coupling 14 is spring loaded by means of elastic members 24, which press the lower end of the tube 16 against two rails 25 which are displaceable laterally by means of an actuation mechanism 26. This mechanism consists of a conical actuation member, the point of which is directed against the space between the laterally displaceable rails. This member is, via a rod 27, connected to a breaking mechanism 28. This later mechanism comprises a retainer 29 for a glass tube 30 and a lever 31, which by means of a spring and the rod 27 are kept in the position shown in FIG. 3. The lever 31 can be pushed down in the direction of the arrow by means of a weight, e.g. a plummit, whereby the glass tube 30 is crushed (broken) and the releasing device 17 is opened and the coupling with the lower gable of the sample receptacle is displaced downwards due to actuation by the elastic members 24.

When the coupling has moved to a level in the vicinity of its downmost position it will hit a lever 32, which via a spring loaded push rod 33 lifts a lock bolt for engagement with a spring loaded locking plunger 34, which is designed so that it exerts a pressure on the tube 20 which is inserted through a hole 35 in the locking device 36, whereby the tube is compressed so the communication with the sample receptacle is interrupted.

The sampling device is preferably suspended from a wire which is preferably attached thereto in such a manner that a plummit can be dropped down along it and hit the lever 31.

For activation of the sampling device at the desired depth, a not shown plummit is thus dropped and will activate the breaking mechanism 28, whereby the glass tube 30 is crushed. The sample tube 20 then will swing out from the sampling device due to its inherent elasticity, at the same time as the releasing device is activated and the lower gable of the sample receptacle 1 is filled with water. At the time the receptacle is full the coupling 14 reaches its bottom position and it will then release the closing mechanism 36 which pinches around the sampling tube and closes it.

When the water collector has been recovered the tube is provided with a tube clasp and the closing mechanism can be disengaged, whereupon the sample receptacle 1 can be released from the bayonet mount 13, and the sample device is ready to be provided with a new sample receptacle for renewed use.

FIG. 4 shows in a side view a modified embodiment of a water collector according to the invention. Corresponding details have been given the same reference numerals as those in the embodiment according to FIGS. 1 to 3. The sample receptacle 1 is the same as that used in the previous embodiment, but shown in folded out position, and it is attached to a sampling device 41, which has means 13 for connection of the upper gable of the receptacle and a coupling 14 corresponding to that of the earlier embodiment. The main difference between this embodiment and that shown in FIG. 3 is that the rubber tube 20 at its end remote from the receptacle in inactive position is closed by being slipped over a sealingly fitting peg 42, which is clearly shown in the detail view of FIG. 5 showing the upper part of the device with some parts in section. This peg 42 is pivotably connected about a shaft 43 fitted on a lever 44, which is arranged to extend over the path of the plummit 45. The plummit 45, when dropped along the wire 46, will hit the lever and move this downwards, whereby the peg 42 simultaneously will move downwards between two wall parts 47, 48. The passage between these walls is at least in the upper part so small that the peg can just pass through and the rubber tube 20 then will be pushed off the peg when this is moved down. The tube is thereby released and can due to its inherent flexibility swing out from the side of the collector. The coupling 14, and the actuation mechanism 26 are simultaneously activated and begin to pull the lower gable of the receptacle 1 downwards whereby water is sucked in through tube 20. The tube 20 is closed off by the locking mechanism 36 in the same manner as earlier mentioned as soon as the receptacle is filled, i.e. as soon as the coupling has reached its lowermost position. The glass tube used for closing the rubber tube 20 in the previous embodiment is in this embodiment replaced by the peg 42, which does not have to be crushed in order to open the communication between the ambient water and the interior of the receptacle. The function is however in all other aspects similar to that of the earlier described embodiment.

The disclosed invention provides a collector at a very low price, which fulfils all the above listed requirements, and the "concertina folding principle" used for the sampling has proven itself to function in a faultless manner.

What we claim is:

1. In a sterile water collector of the type comprising a sampling device and a sample receptacle, which is arranged to be activated by external actuation, whereby an inlet to the evacuated sample receptacle is opened, the improvement wherein the sample receptacle consists of a flexible wall structure located between two rigid end bodies, said bodies arranged upon activation of the sampling device to be displaced by means of an external force in a direction away from each other a certain distance, sample water thereby being sucked into the receptacle and wherein said rigid end bodies of the sample receptacle are an upper and a lower circular gable, the upper one of which is provided with a centrally located inlet, to the outer side of which is connected a flexible sampling tube, and wherein the lower gable is provided with a closing member projecting in a direction towards the inlet of the upper gable and adapted to extend into and seal off the inlet when the sample receptacle is in its evacuated position.

2. A water collector as claimed in claim 1, wherein the closure means are arranged to close the inlet when the rigid end bodies have been displaced as much as possible relative to each other.

3. A water collector as claimed in claim 1, wherein the inlet and the closing member are both designed with complementary conical surfaces.

4. A water collector as claimed in claim 1, wherein the flexible wall structure of the sample receptacle consists of a plastic hose which is attachable to the said end bodies.

* * * * *